United States Patent [19]

Perry et al.

[11] Patent Number: 5,015,184
[45] Date of Patent: May 14, 1991

[54] EVACUATOR TUBE TIP GUARD

[76] Inventors: Lanny Perry, RR, Utica; William G. Thomas, Utica Rte., Hobson, both of Mont. 59452

[21] Appl. No.: 478,440

[22] Filed: Feb. 12, 1990

[51] Int. Cl.⁵ .................. A61C 17/06; A61C 17/14
[52] U.S. Cl. ........................................ 433/93; 433/91
[58] Field of Search ............ 433/91, 93, 94, 116; 604/902; 15/415 R

[56] References Cited

U.S. PATENT DOCUMENTS

| | | | |
|---|---|---|---|
| 3,256,885 | 6/1966 | Higgins et al. | 433/91 X |
| 3,777,756 | 12/1973 | Lohr | 433/91 |
| 4,158,916 | 6/1979 | Adler | 433/91 |
| 4,265,621 | 5/1981 | McVey | 433/91 |

FOREIGN PATENT DOCUMENTS 232234  5/1944  Switzerland .................. 433/93

Primary Examiner—Robert P. Swiatek
Assistant Examiner—Nicholas D. Lucchesi
Attorney, Agent, or Firm—Katherine McGuire

[57] ABSTRACT

A dental saliva ejector tube and/or high volume evacuator tube guard having an annular ring segment for frictional and releasable attachment to the open, free end of the ejector tube or as an integral part of a suction tube, either flexible or rigid. The tube guard includes a pair of symmetrical guard loops lying in spaced, parallel planes each having two opposite ends which integrally extend from the annular ring segment and taper inwardly toward the central axis of the annular ring segment in a direction away from the ejector tube. In the preferred embodiment, the symmetrical guards have substantially straight segments extending between the distal end of the guards and the annular ring segment, forming an acute inner angle with the central axis of the ring segment. A third guard loop lying in a plane substantially perpendicular to the spaced, parallel planes integrally extends from the annular ring segment and loops over the symmetrical guard loops to form a cage-like structure wherein saliva and matter may be easily drawn into the ejector tube through the openings between the guard loops, the guard loops substantially preventing the soft tissues of the inside of the mouth from being drawn in therebetween.

2 Claims, 1 Drawing Sheet

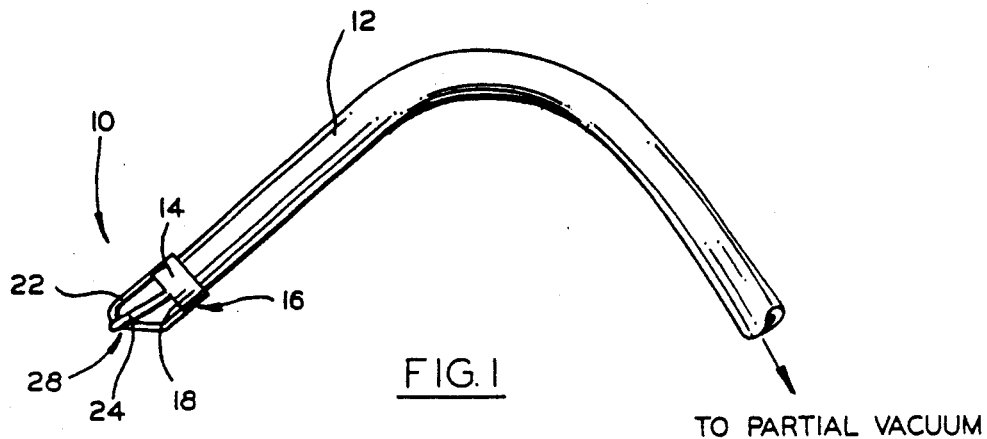
FIG. 1
TO PARTIAL VACUUM
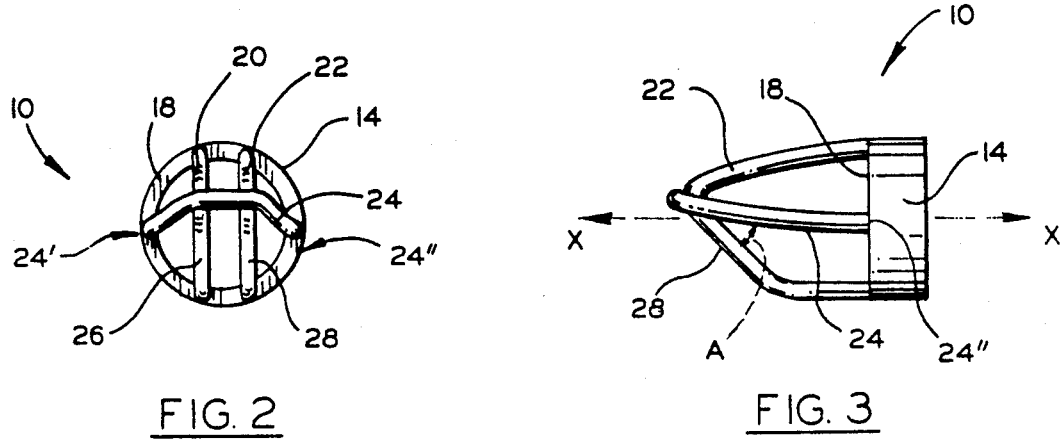
FIG. 2
FIG. 3
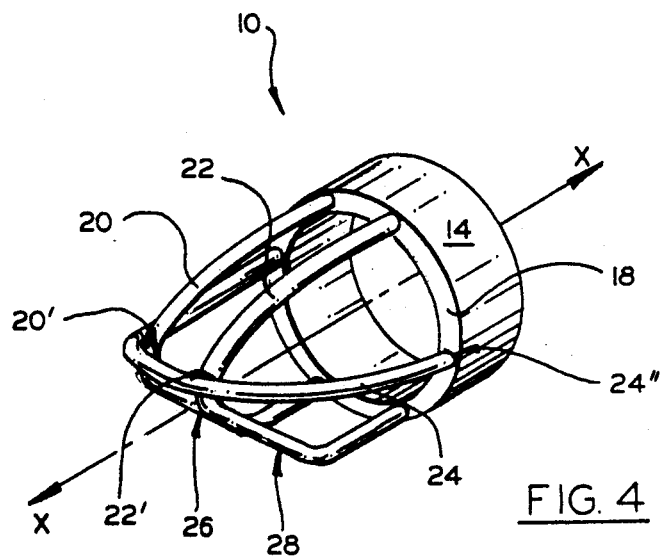
FIG. 4

EVACUATOR TUBE TIP GUARD

BACKGROUND OF THE INVENTION

This invention relates to guards for affixing to the free, open end of a suction tube and, more particularly, to a guard for the open end of suction tubes and high volume evacuators used for ejecting saliva and matter from a patient's mouth during dental procedures.

During certain dental procedures, i.e. procedures which involve the use of modern high speed dental handpieces which eject copious quantities of water for cooling and cleaning, it is necessary to remove the accumulated saliva and matter for effective treatment. This is usually accomplished by the use of a resilient yet flexible suction or ejection tube, the free, open end of which is inserted into the patient's mouth while the opposite end is connected to a source of reduced pressure. To deal with the problem of drawing large debris into the tube and excessive pulling of the soft tissue inside the patient's mouth which may obstruct the tube passageway and cause much discomfort to the patient, guards have been developed which may be inserted over the open end of the tube. Examples of such guards may be seen in U.S. Pat. No. 4,083,115, issued to McKelvey on Apr. 11, 1978; U.S. Pat. No. 2,574,135, issued to Ward on Nov. 6, 1951; and U.S. Pat. No. 3,541,583, issued to Deuschle on Apr. 27, 1967.

Upon inspection, it is seen that the prior art guards all provide a plurality of longitudinally extending radial slots which extend the length of the guard. The annular, proximal end of the guards are telescopically fit over the open end of the suction tube while the distal end tapers inwardly in a direction away from the tube and toward the central, longitudinal axis of the guard and tube to form either a flat or rounded, distal end. The "ribs" which extend from the proximal end to the distal end forming the slots therebetween are typically spaced equally apart from each other and intersect at the central, longitudinal axis of the distal end of the guard to form an "intersection surface" at the distal end with the slots extending from the proximal end to this intersection surface.

During dental procedures, the dentist typically has an assistant standing by to perform saliva ejection on the patient as the dentist works. The suction tube with the guard attached thereto is inserted into the patient's mouth at the locations where the saliva typically accumulates. This may be under the tongue and along the outer gum line of the bottom teeth, between the cheek and teeth. When inserted, the distal end of the guard comes into contact with the soft tissue of the mouth. It is desirous that the suction power of the tube be kept at a minimum operating level such that saliva is effectively withdrawn from the mouth cavity yet the soft, pliant tissues of the mouth are not painfully drawn into the slots of the guard. With the guard thus inserted into the mouth, it is necessary for the assistant to move the tube such that the slot openings come into contact with the saliva to draw it therein since the terminal, distal end of the prior art guards is not open but instead has a surface where the extending "ribs" intersect.

It is therefore a principal object of the present invention to provide a dental suction tube tip guard which provides for maximum withdrawal of saliva and matter entrained therein while the tube is maintained at a suitable, reduced pressure.

It is a further object of the present invention to provide a dental suction tube tip guard which is configured such that the working surface thereof is provided with a maximum open area for passage of saliva and matter therethrough.

It is still another object of the present invention to provide a dental suction tube tip guard which is more efficient in withdrawing saliva and matter from a patient's mouth by providing maximum comfort to the patient through reduced surface area of the guard which permits minimal, required movement of the tube and guard within the mouth.

Other objects will in part be obvious and in part appear hereinafter.

SUMMARY OF THE INVENTION

The invention provides a guard for releasably and frictionally fitting over the open end of a conventional suction tube and/or high volume evacuator used to withdraw excessive saliva and particles entrained therein from the mouth of a patient during dental procedures. It is well known that the soft tissues lining the oral cavity of the mouth are very pliant and sensitive areas of the human body. It is therefore the purpose of the invention to eliminate contact of the stiff, peripheral edge of the open end of the suction tube with the tissues of the mouth and greatly reduce the tendency of the suction tube of pulling at the soft tissue which can be painful and obstruct the tube passageway thereby requiring the dentist to stop his or her dental procedure to dislodge it.

The guard is preferably formed of a rigid material such as medical grade ABS which may be sterilized by known means. The proximal portion of the guard is annularly shaped to substantially the same diameter as the outer diameter of the open end of the suction tube such that the guard may be easily and securely fit over the open end of the suction tube. A pair of substantially symmetrical, elongated "guard loops" lying in substantially parallel, spaced planes extend from the proximal, annular end of the guard and are formed at common angles at their distal portions to define the "working surface" of the guard, i.e., it is the angled portion of the guard loops which come into substantial contact with the soft tissues inside the mouth, drawing saliva and matter in therebetween. A third elongated guard loop lying in a plane substantially perpendicular to the said parallel planes extends from the proximal end of the guard and passes over the distal-most, outer portion of the pair of symmetrical guard loops to stabilize them in their intended position.

It is thus evident that saliva and matter may be drawn into the axial passageway of the suction tube through any or all of the openings defined by the guard loops, the guard openings being significantly larger in area than the solid areas of the three guard loops.

BRIEF DESCRIPTION OF THE DRAWINGS

FIG. 1 is a side elevational view of the suction guard mounted to a typical dental suction tube;

FIG. 2 is an end view of the distal end of the suction guard;

FIG. 3 is a side elevational view thereof; and

FIG. 4 is a perspective view thereof.

DETAILED DESCRIPTION

Referring now to the drawings, there is seen in the various figures the preferred embodiment of the invention, denoted generally by the reference numeral 10. The invention comprises a guard 10 for releasable attachment to the free, open end of a conventional suction tube used for withdrawing saliva and matter from a patient's mouth during routine dental procedures, an example of such a suction tube denoted by reference numeral 12 in FIG. 1. It is contemplated that the guard 10 may also be used for similar tubes used either for applying or removing liquids to and from various body cavities in the medicinal treatment art. Suction tube 12 is typically rigid for ease of handling by the dental auxiliary, and made of a somewhat rigid material such as ABS or stainless steel, making the free, open end thereof unpleasant for direct contact with the soft, sensitive tissues lining the inside of the mouth. Absent some type of guard, such as the guard 10, the very pliant tissues of the mouth tend to be drawn up into the tube 12, obstructing the continued withdrawal of saliva and matter until dislodged therefrom. This usually requires discontinuance of the dental procedure to dislodge the tube from the skin in addition to the discomfort to the patient. Accordingly, guard 10 provides a working surface which will not irritate the soft tissues of the mouth nor will it allow the same to be drawn into tube 12 to obstruct the withdrawal of saliva and matter therethrough. This design also allows for the passage of large particles of old filling and tooth matter, without removal of the tip.

Guard 10 is configured with proximal, annular ring segment 14 such that it may be easily and quickly frictionally attached to and removed from the free, open end 16 of tube 12 by the user of the instrument. As aforementioned, it is desired that guard 10 be formed of a rigid material such as medical grade ABS or the like. It is also contemplated that guard 10 may be formed integrally with free end 16 of tube 12 instead of being a separate, releasably attached piece as shown in the drawings.

Annular ring segment 14 should be formed such that it has an inner diameter which is substantially the same as the outer diameter of free end 16 of tube 12. In this way, guard 10 may be releasably attached to tube 12 by telescopically inserting free end 16 of tube 12 into ring segment 14, preferably until open end 16 of tube 12 reaches the distal edge 18 of ring segment 14. It is noted that depending on the costs of materials used and the method of fabrication of guard 10, it may be a piece which is meant to be disposed of after a single use, or it may be preferred that guard 10 be kept and sterilized after each use by known means.

As best seen in FIGS. 2 and 4, a pair of rigid guard loops 20 and 22 integrally extend from the distal edge 18 of ring segment 14 and lie in parallel, spaced planes. A third guard loop 24 integrally extends from two opposite points 24' and 24" along distal edge 18, looping over the outer, distal-most edges 20' and 22' of guard loops 20 and 22. As seen, guard loop 24 lies in a plane which is substantially perpendicular to the spaced, parallel planes in which loops 20 and 22 lie, thereby forming a somewhat cage-like structure. Guard loops 20 and 22 include substantially straight segments 26 and 28, respectively, which form an acute, inner angle A with the longitudinal axis x—x of guard 10 as seen in FIG. 3. Straight segments 26 and 28 provide the "working surface" of guard 10, i.e., segments 26 and 28 are the primary parts of guard 10 to come into contact with the soft tissues lining the inside of the mouth.

As seen in FIG. 1, guard 10 is attached to tube 12 such that straight segments 26 and 28 of guard loops 20 and 22 form the bottom-most portion of guard 10 when tube 12 is manually grasped in the intended manner. With guard 10 thus frictionally secured and positioned on tube 12, guard 10 is inserted into the mouth of the patient, lightly contacting segments 26 and 28 with the lining of the mouth where excessive saliva and matter has accumulated, typically under or beside the tongue and in the trough formed by dental ridge and the cheek. While any pulling of the soft tissue of the mouth into the axial passageway of tube 12 is substantially prevented by guard loops 20, 22 and 24, saliva and small particles entrained therein are easily passed through the openings formed between the guard loops and are allowed to be withdrawn and ejected from the mouth. As can be appreciated more fully by a perusal of the drawings, the openings between the guard loops 20, 22 and 24, which provide communication between the mouth and the axial passageway of tube 12, are significantly larger in area (i.e., open area) than the sum of the area of the guard loops (i.e., closed area). This provides for maximum withdrawal of saliva and matter from a patient's mouth under a partial vacuum of tube 12.

What is claimed is:

1. A guard for attachment to the open, free end of a dental saliva ejector tube, and/or a high volume evacuator tube, said guard comprising:

(a) a proximal, annular ring segment having a central, longitudinal axis for engagement with said open, free end; and (b) at least two rigid guard loops of substantially like configuration and occupying a finite area, each of said guard loops having first and second ends which integrally extend from said annular ring segment along first and second lengths which slant inwardly toward said axis in a direction away from said ejector tube to form arcuate, distal portions at the intersection of said first and second lengths, said intersection of each said guard loop first and second lengths lying adjacent said central, longitudinal axis, said guard loops lying in substantially parallel, spaced planes to define openings therebetween communicating with said ejector tube open end, said openings having a total area greater than said finite area occupied by said guard loops and wherein said first length of each of said at least two guard loops slants gradually inwardly toward said central longitudinal axis and said second length of each of said at least two guard loops extends linearly and parallel to said central, longitudinal axis from said second end for substantially a first half of said second length, and wherein the second half of said second length, which extends between said first half and said arcuate, distal portion, is linear and forms an inner, obtuse angle with said first half, and an inner, acute angle with said central, longitudinal axis at said distal portion.

2. The invention according to claim 1 wherein said guard further comprises a rigid stabilizer loop which lies in a plane substantially perpendicular to said parallel, spaced planes, said stabilizer loop having two opposite ends integrally extending from substantially opposite sides of said annular ring segment and slanting gradually inwardly toward said central longitudinal axis in a direction away from said ejector tube to form an arcuate, distal end which lies adjacent said arcuate, distal portions of said at least two guard loops to further divide said openings and wherein the sum of the area of said stabilizer loop and said finite area of said at least two guard loops is less than the area of said further divided openings.

* * * * *